(12) United States Patent
Kishima

(10) Patent No.: US 11,452,453 B2
(45) Date of Patent: Sep. 27, 2022

(54) IMAGE PROCESSING APPARATUS, IMAGE PROCESSING METHOD, INFORMATION PROCESSING PROGRAM, FLUORESCENCE OBSERVATION SYSTEM, AND FLUORESCENCE NAVIGATION SURGERY SYSTEM

(71) Applicant: Sony Corporation, Tokyo (JP)

(72) Inventor: Koichiro Kishima, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 847 days.

(21) Appl. No.: 16/163,285

(22) Filed: Oct. 17, 2018

(65) Prior Publication Data

US 2019/0046041 A1    Feb. 14, 2019

Related U.S. Application Data

(63) Continuation of application No. 14/222,162, filed on Mar. 21, 2014, now Pat. No. 10,143,378.

(30) Foreign Application Priority Data

Mar. 29, 2013  (JP) .............................. JP2013-074785

(51) Int. Cl.
*A61B 5/00* (2006.01)
*G06T 7/00* (2017.01)
*G06T 7/30* (2017.01)

(52) U.S. Cl.
CPC ............ *A61B 5/0071* (2013.01); *A61B 5/742* (2013.01); *G06T 7/30* (2017.01); *G06T 7/0012* (2013.01);
(Continued)

(58) Field of Classification Search
None
See application file for complete search history.

(56) References Cited

U.S. PATENT DOCUMENTS 3,971,065 A * 7/1976 Bayer ................ H04N 9/04557
                                                    348/276
4,817,433 A    4/1989 Sato
(Continued)

FOREIGN PATENT DOCUMENTS

| JP | 2001-299676 | 10/2001 |
|----|-------------|---------|
| JP | 2005-346552 | 12/2005 |
| JP | 4745059     | 5/2011  |

OTHER PUBLICATIONS

Troyan et al., "The FLARE Intraoperative Near-Infrared Fluorescence Imaging System: A First-in-Human Clinical Trial in Breast Cancer Sentinel Lymph Node Mapping," Official Journal of the Society of Surgical Oncology, Society of Surgical Oncology, 2009, 10 pages.

(Continued)

*Primary Examiner* — Luther Behringer
(74) *Attorney, Agent, or Firm* — Sheridan Ross P.C.

(57) ABSTRACT

An information processing apparatus includes a storage unit, a cutting-out unit, and a display controller. The storage unit is configured to store an image of fluorescence emitted from an observation target area of a living body in a recording medium as a fluorescence image of the observation target area, the image of fluorescence being captured with a first definition, the image of fluorescence being obtained by applying excitation light to the observation target area to which a fluorescent reagent is added in advance.
The cutting-out unit is configured to cause a user to select at least a partial area of the fluorescence image and to cut out the selected area as a fluorescence image of a ROI area. The display controller is configured to cause a display unit to display the fluorescence image of a ROI area with a second definition that is lower than the first definition.

6 Claims, 5 Drawing Sheets

(52) U.S. Cl.
CPC ............... *G06T 2207/10064* (2013.01); *G06T 2207/20104* (2013.01); *G06T 2207/20221* (2013.01); *G06T 2207/30004* (2013.01)

(56) References Cited

U.S. PATENT DOCUMENTS

| | | | |
|---|---|---|---|
| 5,740,267 A * | 4/1998 | Echerer | G06T 5/009 |
| | | | 382/132 |
| 5,980,458 A | 11/1999 | Clark | |
| 6,146,329 A | 11/2000 | Hayakawa | |
| 6,217,510 B1 * | 4/2001 | Ozawa | A61B 1/00091 |
| | | | 600/128 |
| 6,229,910 B1 | 5/2001 | Kaneko | |
| 6,960,165 B2 * | 11/2005 | Ueno | A61B 1/00009 |
| | | | 600/109 |
| 7,194,118 B1 | 3/2007 | Harris et al. | |
| 10,143,378 B2 | 12/2018 | Kishima | |
| 2002/0102101 A1 | 8/2002 | Pelletier | |
| 2002/0138008 A1 * | 9/2002 | Tsujita | A61B 1/05 |
| | | | 600/473 |
| 2003/0229270 A1 * | 12/2003 | Suzuki | G02B 23/2469 |
| | | | 600/178 |
| 2004/0109231 A1 | 6/2004 | Haisch et al. | |
| 2009/0021578 A1 * | 1/2009 | Yamazaki | H04N 5/217 |
| | | | 348/65 |
| 2014/0049626 A1 | 2/2014 | Ishihara | |
| 2014/0369564 A1 | 12/2014 | Chono | |

OTHER PUBLICATIONS

Urano et al., "Selective molecular imaging of viable cancer cells with pH-activatable fluorescence probes," January National Institute of Health, 2009, 16 pages.
Urano et al., "Development of Fluorescent Reagent That Enables Cancer Cell To Be Brightened Only by Spraying," 8 pages.
Official Action for U.S. Appl. No. 14/222,162, dated Jul. 14, 2016, 15 pages.
Official Action for U.S. Appl. No. 14/222,162, dated Jan. 26, 2017, 16 pages.
Official Action for U.S. Appl. No. 14/222,162, dated Jun. 29, 2017, 15 pages.
Official Action for U.S. Appl. No. 14/222,162, dated Jan. 17, 2018, 10 pages.
Notice of Allowance for U.S. Appl. No. 14/222,162, dated Jul. 16, 2018, 11 pages.

* cited by examiner

IMAGE PROCESSING APPARATUS, IMAGE PROCESSING METHOD, INFORMATION PROCESSING PROGRAM, FLUORESCENCE OBSERVATION SYSTEM, AND FLUORESCENCE NAVIGATION SURGERY SYSTEM

CROSS REFERENCE TO RELATED APPLICATIONS

This application is a continuation of U.S. patent application Ser. No. 14/222,162, filed Mar. 21, 2014, now U.S. Pat. No. 10,143,378, which claims the benefit of Japanese Priority Patent Application JP 2013-074785 filed Mar. 29, 2013, the entire contents of which are incorporated herein by reference.

BACKGROUND

The present disclosure relates to a fluorescence navigation surgery system for performing fluorescence navigation surgery as surgery, an image processing apparatus used therefor, an image processing method, an information processing program, and a fluorescence observation system.

In the past, a dissection of a sentinel lymph node that is suspected to be a metastasis has been performed in ablative surgery of a breast cancer. When the dissection of a sentinel lymph node that is not easily identified by visual inspection is performed, the sentinel lymph node is identified by using indocyanine green (ICG) being a fluorescent reagent.

Examples of a method of identifying a sentinel lymph node using ICG include a method of applying excitation light in a near infrared wavelength band to an observation area and capturing an image of fluorescence emitted from the ICG in a near infrared wavelength band to observe the image (see, for example, Japanese Patent Application Laid-open No. 2001-299676).

Examples of a commercialized system for observing an image of fluorescence emitted from an ICG reagent for identifying a sentinel lymph node include pde-neo (manufactured by Hamamatsu Photonics K.K., see Japanese Patent No. 4745059), HyperEye Medical System (manufactured by MIZUHO Co., Ltd.), and mini-FLARE (Beth Israel hospital, see Annals of Surgical Oncology 2009 October; 16(10): 2943-2952, the Internet <URL:http://www.ncbi.nlm.nih.gov/pmc/articles/PMC2772055/>).

The HyperEye Medical System and the mini-FLARE have functions such as superimposing a fluorescence observation image on a visible light observation image captured by a built-in video camera for visible light image observation to display the superimposed image. In order to perform the superimposition of the images appropriately, for example, in the mini-FLARE system, the video camera for visible light image observation and a video camera for fluorescence image observation are configured to share the same zoom lens used for imaging so that the field of view of both images is the same, and to include a respective imaging device having the same number of pixels.

Moreover, with progress in cancer gene research and reagent research in recent years, it is becoming possible to selectively stain cancer cells (see, for example, research by Hisataka Kobayashi, Nature Medicine 15, 104-109 (2009)). For example, a fluorescent reagent that causes cancer cells to glow only by spraying has been developed (see the press release "fluorescent reagent that causes cancer cells to glow only by spraying has been developed," [online], Nov. 24, 2011, Japan Science and Technology Agency [searched on Mar. 18, 2013], the Internet <URL:http://www.jst.go.jp/pr/announce/20111124-2/index.html>).

Moreover, in the past, measures against a medical malpractice suit by, during surgery, capturing an image of the surgery with a video camera and storing the image, in medical practice, have been considered. Then, an image of a surgical field with a high definition (HD) is obtained to capture an image of the surgical technique, and images of a surgical table and the periphery of the surgical table (with a standard definition (SD) or HD) are obtained to capture an image of the whole of the surgery (see, for example, Japanese Patent Application Laid-open No. 2005-346552).

SUMMARY

In the case where the reagent that selectively stains cancer cells is used to detect cancer cells, it is important to observe the entire surgical field including not only an area that is focused on by an operator during a surgical operation, i.e., an area to be removed with a scalpel or the like, but also areas other than the area. This is because there is a need to confirm, during or after the surgery, whether or not cancer cells that have not been removed exist.

However, the systems such as the pde-neo, the HyperEye Medical System, and the mini-FLARE are based on the assumption that the zoom lens of the video camera that captures an image is used to adjust the size of the field of view observed by the operator. Specifically, a fluorescence observation image captured during surgery includes only an area of the surgical field in which the operator is interested. Therefore, it has been difficult to use the fluorescence observation image captured with the system to prove that there is no unremoved cancer cell.

In addition, in the existing system, the fluorescence image is not necessarily captured, displayed, and stored appropriately.

In view of the circumstances as described above, it is desirable to provide an image processing apparatus, an image processing method, an information processing program, a fluorescence observation system, and a fluorescence navigation surgery system, which are capable of capturing, displaying, and storing a fluorescence image appropriately.

According to an embodiment of the present disclosure, there is provided an information processing apparatus including a storage unit configured to store an image of fluorescence emitted from an observation target area of a living body in a recording medium as a fluorescence image of the observation target area, the image of fluorescence being captured with a first definition, the image of fluorescence being obtained by applying excitation light to the observation target area to which a fluorescent reagent is added in advance, a cutting-out unit configured to cause a user to select at least a partial area of the fluorescence image and to cut out the selected area as a fluorescence image of a ROI area, and a display controller configured to cause a display unit to display the fluorescence image of a ROI area with a second definition that is lower than the first definition.

In the present disclosure, a fluorescence image of the entire observation target area is stored with the first definition and the display unit is caused to display the fluorescence image of the ROI area selected by the user is displayed with the second definition for a surgical operation. Therefore, the two purposes of the storing and the observation are achieved, and a fluorescence image can be captured, displayed, and stored appropriately.

In the information processing apparatus according to this embodiment, the storage unit may be configured to store RAW image data of the fluorescence image of the observation target area as it is.

According to an embodiment of the present disclosure, there is provided an image processing method including storing an image of fluorescence emitted from an observation target area of a living body in a recording medium as a fluorescence image of the observation target area, the image of fluorescence being captured with a first definition, the image of fluorescence being obtained by applying excitation light to the observation target area to which a fluorescent reagent is added in advance, causing a user to select at least a partial area of the fluorescence image and cutting out the selected area as a fluorescence image of a ROI area, and causing a display unit to display the fluorescence image of a ROI area with a second definition that is lower than the first definition.

According to an embodiment of the present disclosure, there is provided an information processing program that causes a computer to function as a storage unit configured to store an image of fluorescence emitted from an observation target area of a living body in a recording medium as a fluorescence image of the observation target area, the image of fluorescence being captured with a first definition, the image of fluorescence being obtained by applying excitation light to the observation target area to which a fluorescent reagent is added in advance, a cutting-out unit configured to cause a user to select at least a partial area of the fluorescence image and to cut out the selected area as a fluorescence image of a ROI area, and a display controller configured to cause a display unit to display the fluorescence image of a ROI area with a second definition that is lower than the first definition.

According to an embodiment of the present disclosure, there is provided a fluorescence observation system including an excitation light source configured to apply excitation light to an observation target area of a living body to which a fluorescent reagent is added in advance, an imaging unit configured to capture an image of fluorescence emitted from the observation target area with a first definition as a fluorescence image of the observation target area, a storage unit configured to store the fluorescence image of the observation target area in a recording medium, a cutting-out unit configured to cause a user to select at least a partial area of the fluorescence image and to cut out the selected area as a fluorescence image of a ROI area, and a display unit configured to display the fluorescence image of a ROI area with a second definition that is lower than the first definition.

According to an embodiment of the present disclosure, there is provided a fluorescence navigation surgery system including an excitation light source configured to apply excitation light to an observation target area of a living body to which a fluorescent reagent is added in advance, a fluorescence imaging unit configured to capture an image of fluorescence emitted from the observation target area with a first definition as a fluorescence image of the observation target area, a storage unit configured to store the fluorescence image of the observation target area in a recording medium, a cutting-out unit configured to cause a user to select at least a partial area of the fluorescence image and to cut out the selected area as a fluorescence image of a ROI area, a fluorescence image display unit configured to display the fluorescence image of a ROI area with a second definition that is lower than the first definition, a visible light imaging unit configured to cause the user to select at least a partial area of the observation target area and to capture an image of the selected area as a visible light image, and a visible light image display unit configured to display the visible light image.

According to an embodiment of the present disclosure, there is provided a fluorescence navigation surgery system including an excitation light source configured to apply excitation light to an observation target area of a living body to which a fluorescent reagent is added in advance, a fluorescence imaging unit configured to capture an image of fluorescence emitted from the observation target area with a first definition as a fluorescence image of the observation target area, a storage unit configured to store the fluorescence image of the observation target area in a recording medium, a visible light imaging unit configured to select at least a partial area of the observation target area as a ROI area based on information on a selected position input by a user and to capture a visible light image of the ROI area, a cutting-out unit configured to cut out a fluorescence image of the ROI area from the fluorescence image of the observation target area based on the information on a selected position, a superimposing unit configured to generate a superimposed image by aligning a position of the visible light image with a position of the cut fluorescence image and superimposing the images, and a superimposed image display unit configured to display the superimposed image with a second definition that is lower than the first definition.

According to an embodiment of the present disclosure, there is provided a fluorescence navigation surgery system including an excitation light source configured to apply excitation light to an observation target area of a living body to which a fluorescent reagent is added in advance, a fluorescence imaging unit configured to capture an image of fluorescence emitted from the observation target area with a first definition as a fluorescence image of the observation target area, a storage unit configured to store the fluorescence image of the observation target area in a recording medium, a visible light imaging unit configured to cause a user to select at least a partial area of the observation target area and to capture a visible light image of the selected area as a ROI area, a cutting-out unit configured to cut out a fluorescence image of the ROI area from the fluorescence image of the observation target area based on edge information included in the visible light image, a superimposing unit configured to generate a superimposed image by aligning a position of the visible light image with a position of the cut fluorescence image and superimposing the images, and a superimposed image display unit configured to display the superimposed image with a second definition that is lower than the first definition.

As described above, according to the present disclosure, it is possible to capture, display, and store a fluorescence image appropriately.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, embodiments of the present disclosure will be described with reference to the drawings.

First Embodiment (Entire Configuration)

Figure 1:
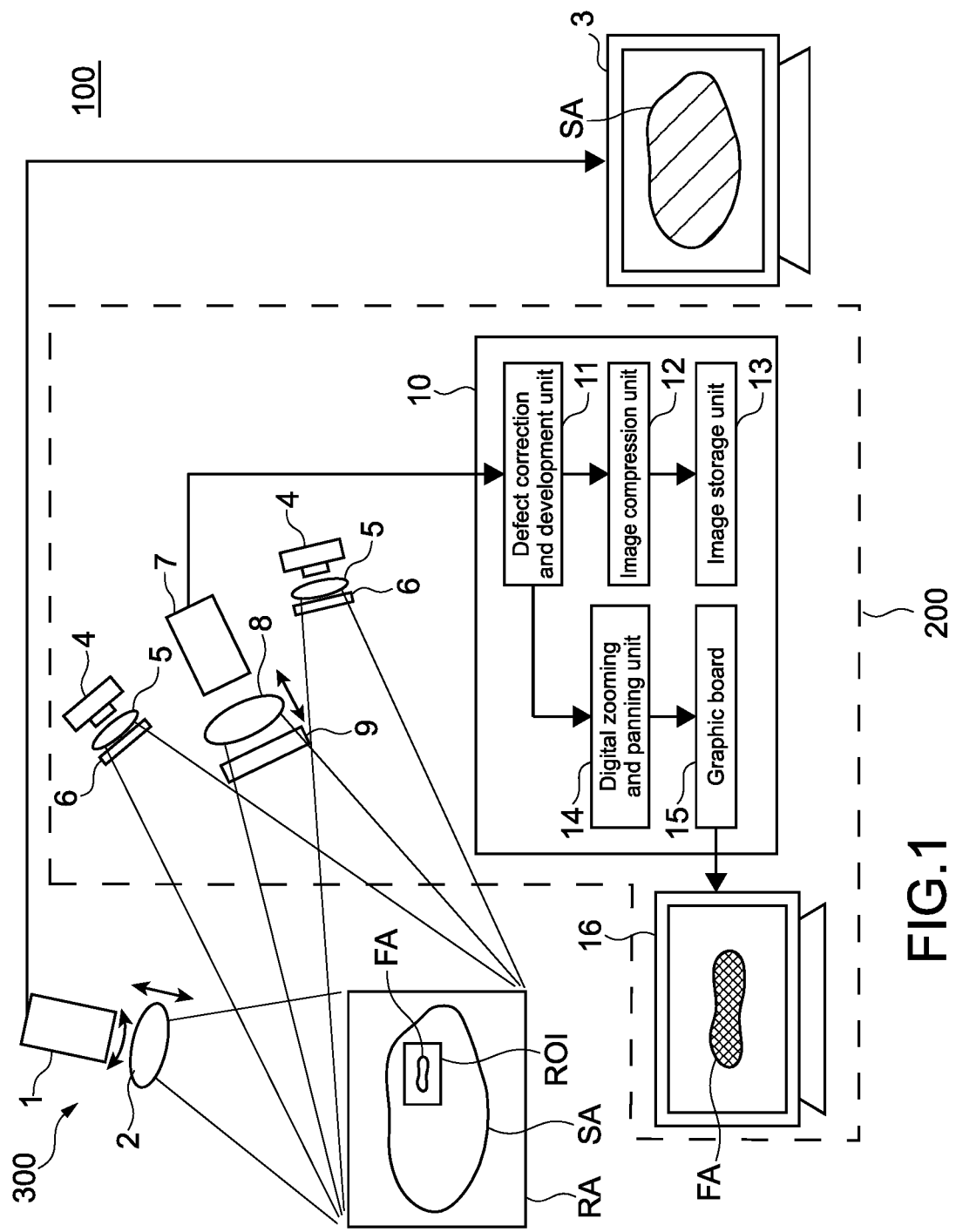
FIG. 1 is a whole configuration diagram of a fluorescence navigation surgery system 100 according to a first embodiment.

The entire configuration of a fluorescence navigation surgery system according to a first embodiment will be described first. FIG. 1 is a whole configuration diagram of the fluorescence navigation surgery system 100 according to this embodiment.

The fluorescence navigation surgery system 100 is largely divided into a visible light capturing system 300 for an operator to observe the surgical field SA and a fluorescence capturing system 200 that captures, stores, and displays a fluorescence image. Since the fluorescence navigation surgery system 100 is divided into the visible light capturing system 300 and the fluorescence capturing system 200, zoom lenses of the capturing systems can be operated independently unlike the above-mentioned system such as the mini-FLARE, which shares the same zoom lens.

(Visible Light Capturing System)

The visible light capturing system 300 is configured to include a video camera for surgical field observation 1, an optical zoom lens 2, and a monitor for surgical field observation 3. The video camera for surgical field observation 1 is capable of capturing an image of the entire surgical field SA, and the capturing direction thereof can be rotated, i.e., the video camera can be panned. Further, the video camera for surgical field observation 1 can perform optical zooming with the optical zoom lens 2 to capture an image of only an area ROI in which the operator is interested. Because the video camera for surgical field observation 1 needs to capture an image of the operator's handling of a needle accurately, it is expected to output an image at a high frame rate. It should be noted that the area ROI in which the operator is interested represents an area he/her is thinking about trying to remove or an area that has been removed.

The monitor for surgical field observation 3 is configured to display an image with an HD. As shown in FIG. 1, the entire surgical field SA is displayed on the monitor for surgical field observation 3, for example. In the case where the fluorescence wavelength is a near-infrared wavelength that is not in a visible light band, the fluorescence area FA is not displayed on the monitor for surgical field observation 3. It should be noted that the visible light capturing system 300 is used mainly in the case of endoscopic surgery and is not used in the case of general abdominal surgery or open heart surgery in some cases.

(Fluorescence Capturing System)

On the other hand the fluorescence capturing system 200 is configured to include an LED 4, a lens 5, an exciting filter 6, a 24M pixel camera 7, an optical zoom lens 8, an emission filter 9, an image processing apparatus 10, and a monitor for fluorescence image observation 16. The LED 4, the lens 5, and the exciting filter 6 constitute an excitation light source. It should be noted that the fluorescence capturing system 200 may have the same size and shape as that of the above-mentioned pde-neo or mini-FLARE in the case of general abdominal surgery or open heart surgery, and may have a size that can be integrated into a laparoscope or an endoscope in the case of laparoscopic surgery or endoscopic surgery, respectively.

Moreover, the image processing apparatus 10 is configured to include a defect correction and development unit 11, an image compression unit 12, an image storage unit 13, the digital zooming and panning unit 14, and a graphic board 15.

The image processing apparatus 10 is constituted of hardware elements of a personal computer (PC) including, for example, a CPU (Central Processing Unit), a ROM (Read Only Memory), and a RAM (Random Access Memory). Alternatively, the image processing apparatus 10 may be constituted of a dedicated IC such as an FPGA (Field Programmable Gate Array).

The image processing apparatus 10 exchanges various signals with the defect correction and development unit 11, the image compression unit 12, the image storage unit 13, the digital zooming and panning unit 14, and the graphic board 15 and executes various types of arithmetic processing to process a fluorescence image. Various programs and various types of data for the various types of arithmetic processing are loaded to the RAM. The CPU executes the programs loaded to the RAM. The ROM stores the programs and data loaded to the RAM.

It should be noted that the CPU executes the program loaded to the RAM from the ROM or the like, and thus functional blocks of the defect correction and development unit 11, the image compression unit 12, the image storage unit 13, and the digital zooming and panning unit 14 are achieved.

(Details of Elements and Flow of Processing)

First, in the fluorescence capturing system 200, excitation light is applied to the surgical field SA by LED illumination including the LED 4, the lens 5, and the exciting filter 6.

A fluorescent contrast medium such as ICG is locally injected or sprayed in the surgical field SA in advance and thus is collected at the desired place. The excitation light applied to the surgical field SA causes the fluorescent contrast medium to glow (hereinafter, the area that glows, on which the fluorescent contrast medium collects, being referred to as fluorescence area FA).

The fluorescence emitted from the fluorescence area FA is transmitted through the emission filter 9, and an image of the fluorescence is enlarged by the optical zoom lens 8 and is captured by the 24M pixel camera 7. The emission filter 9 plays a role of blocking light having a wavelength other than that of the target fluorescence. The optical zoom lens 8 plays a role of adjusting the field of view by the 24M pixel camera 7 so that an image of an entire image storing area RA that may undergo surgery is captured.

The 24M pixel camera 7 is the most important element in the present disclosure, has 24M pixels, and includes an imaging device that is capable of capturing an image with an ultra-high definition of 6 k×4 k, for example. From the imaging device, an image can be output at the rate of up to 6.3 fps, for example. Because the 24M pixel camera 7 does not capture an image of a movable object such as handling of a needle but capture an image of an object that does not move such as cancer cells emitting fluorescence unlike the video camera for surgical field observation 1, it only needs to have a frame rate from 1 fps to 3 fps.

The fluorescence image output from the 24M pixel camera 7 is input to the image processing apparatus 10. The fluorescence image input to the image processing apparatus 10 is subject to development processing such as defect correction processing and demosaic processing in the defect correction and development unit 11, first. After the development processing, the fluorescence image is output to the image compression unit 12 and the digital zooming and panning unit 14.

The fluorescence image input to the image compression unit 12 is compressed through image compression processing and thus the image size is reduced. After that, the compressed fluorescence image is output to the image storage unit 13.

Figure 2:
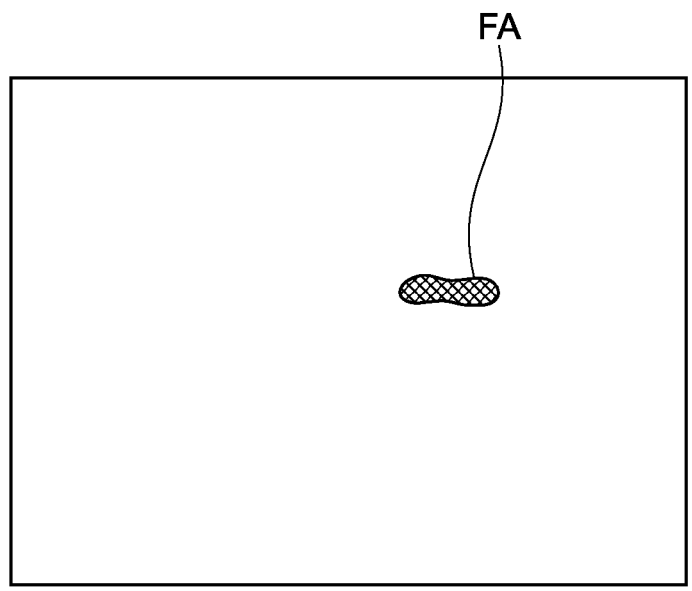
FIG. 2 is a diagram showing an image of an entire surgical field SA in which only a fluorescence area FA glows.

After the image compression, the fluorescence image input to the image storage unit 13 is stored in the image storage unit 13. The image storage unit 13 includes a storage medium such as an HDD (hard disk drive), and the compressed fluorescence image is stored in the storage medium. The image stored in the storage medium is, for example, an image of the entire surgical field SA in which only the fluorescence area FA glows, which is shown in FIG. 2.

After the development processing, the digital zooming and panning unit 14 performs digital zooming processing or panning processing on the fluorescence image output to the digital zooming and panning unit 14 to enlarge an image of only the area ROI in which the operator is interested and to display the image.

Further, the digital zooming and panning unit 14 may perform small pixilation processing to clearly display a fluorescence image of only the area ROI in which the operator is interested, i.e., display the image pixel by pixel on the monitor for fluorescence image observation 16.

The fluorescence image that has been subject to the processing in the digital zooming and panning unit 14 is displayed on the monitor for fluorescence image observation 16 via the graphic board 15. The monitor for fluorescence image observation 16 is configured to display an image with an HD. As shown in FIG. 2, on the monitor for fluorescence image observation 16, the area ROI including the fluorescence area FA, in which the operator is interested, is enlarged and displayed, for example.

(Fluorescence Image to be Stored and Fluorescence Image to be Displayed)

The present disclosure has a feature that an image stored to prepare for a medical malpractice suit or the like is different from an image displayed on the monitor for fluorescence image observation 16 to be referred to by an operator during a surgical operation. Specifically, the area ROI in which the operator is interested is displayed on the monitor for fluorescence image observation 16, but the image stored in the image storage unit 13 is obtained by capturing an image of the entire surgical fields SA, in which the field of view is adjusted by the optical zoom lens 8.

The image stored in the image storage unit 13 is obtained not by capturing an image of only the area ROI in which the operator is interested in at the time of surgery but by capturing a fluorescence image of the entire surgical field SA. Therefore, after surgery, it is possible to confirm whether or not there is an unremoved portion of the area including, for example, cancer, which is fluorescent-labeled during the surgery.

(Comparison with Typical Technique)

In the above-mentioned typical technique, the imaging device included in the camera that captures an image has a high definition of 2M pixels even if the imaging device is a high-definition one. For that reason, even if an image of the entire surgical field SA is enlarged by digital zooming and only the area ROI in which the operator is interest is extracted as in the present disclosure, the image quality is deteriorated and thus the image is not suitable for practical use. Therefore, it has no choice but to capture an image of only the area in which the operator is interested during surgery, and it may be impossible to capture an image of the entire surgical field SA for confirming whether there is an unremoved portion including, for example, cancer after surgery.

Moreover, in the case where an image of the surgical field SA having a size of, for example, about 15 cm×10 cm is captured using an imaging device having about 2M pixels, the pixel resolution of the imaging device is about 75 µm. Specifically, because the resolution is several times larger than the size of a cell, cancer cells are highly likely to be missed in the confirmation of unremoved cancer cells.

However, in the case where the 24M pixel imaging device used in the embodiment of the present disclosure is used to capture an image of the surgical field SA having a size of about 15 cm×10 cm, the pixel resolution of the imaging device is about 25 µm. Because the resolution of almost the same size of a cancer cell can be achieved, it is possible to store a fluorescence image with a definition in which cancer cells or the like fluorescent-labeled are hard to be missed.

Moreover, in this embodiment, an image of the surgical field SA having a size of, for example, about 15 cm×10 cm captured using the 24M pixel imaging device is subject to digital zooming processing, and the area ROI in which the operator is interested having a size of, for example, about 5 cm×2.5 cm is enlarged and displayed. Even in this case, because the image can be displayed on the monitor for fluorescence image observation 16 with a definition of not less than a pixel by pixel definition, it is possible to provide a fluorescence image with favorable quality to the operator.

(Regarding Size of Surgical Filed and Number of Pixels of Imaging Device)

Now, the relationship between the size of the surgical field SA whose image is captured and the number of pixels of the imaging device that captures a fluorescence image will be described.

For example, in an ovariectomy using a laparoscope in obstetrics and gynecology department, because the observation field of view is adjusted so that a clamp and a needle used in the handling of a needle do not move out of the field of view, the field of view whose image is captured is generally set to be about 7 to 8 cm square or a little more than that.

Then, in order not to miss a tumor having a size of about 100 µm, it is desirable to use an optical system having a pixel resolution of about 50 µm or less to capture a fluorescence image.

In the case where an image of the surgical filed SA having a size of 7 cm on a side with a pixel resolution of 50 µm is captured, the number of pixels of the imaging device is 1400. Therefore, in the case of surgical field SA having a size of about 10 cm on a side, it is desirable to use an imaging device having not less than 2000 pixels on the short side in order to achieve the above-mentioned effects of the present disclosure.

(Regarding Effects of Present Disclosure)

The fluorescence navigation surgery system according to this embodiment is capable of enlarging an image of the area ROI in which the operator is interested by digital zooming in response to a user's request and displaying the image, and capturing and storing an image of the entire surgical filed SA with a pixel resolution in which a tumor is not missed. Therefore, it is possible to capture an image of an area in which the operator is not interested, which is not captured in the typical system, and to store the image. Therefore, it is possible to prepare for a market of countermeasures against a medical malpractice suit, for example.

(Modified Example (Regarding Configuration in which Image is not Compressed when being Stored))

Next, a modified example of the method of storing, in the image storage unit 13, a fluorescence image captured by the 24M pixel camera 7 will be described.

In the above-mentioned embodiment, the fluorescence image is developed in the defect correction and development unit 11 and then is compressed in the image compression unit 12. However, in the case where the deterioration of the image due to the compression is expected to be avoided, the fluorescence image is not compressed and is stored. In this regard, in this modified example, RAW image data output from the 24M pixel camera 7 is not compressed and is stored in the image storage unit 13.

In general, in a color imaging device in which color filters of colors of red, green, and blue (RGB) are arranged in a Bayer pattern on a single plate, RAW image data is output, the output RAW image data is developed, and thus a final color image can be obtained. The size of the color image obtained through the development processing is significantly larger than that of the original RAW image data.

For example, the size of RAW image data output from an imaging device having 24M pixels is about 50 MB in the case where luminance information is 14 bits. If the RAW image data is developed into a color image whose luminance information is 16 bits, the size is 147 MB. Then, even if the luminance information of the developed color image is reduced to 8 bits, the image still has a size of about 73 MB.

As described above, the original RAW image data has a smaller size than the color image whose luminance information is reduced from 16 bits to 8 bits. Therefore, in the case where the image is not compressed and is stored, it is possible to store the image with a small data size when the RAW image data before development is stored as it is. Then, because the capacity of the storage medium that is necessary to store a fluorescence image can be reduced in the image storage unit 13, it is efficient from a view point of a cost of system operation.

Figure 3:
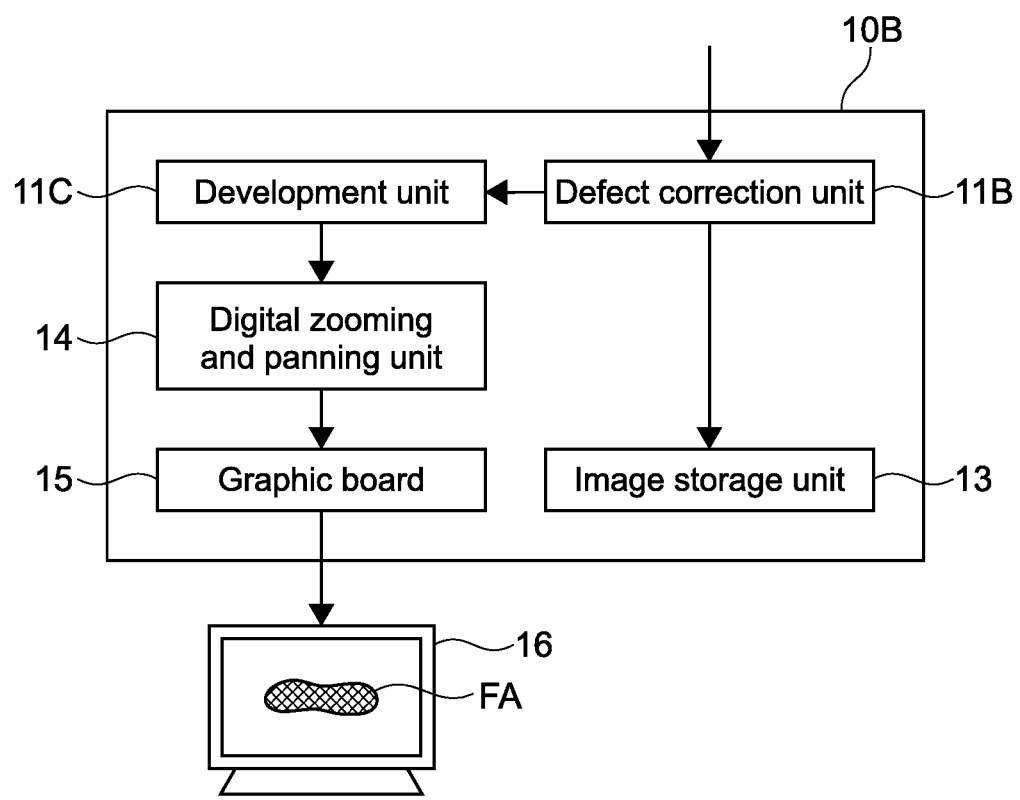
FIG. 3 is a diagram showing functional blocks of an image processing apparatus 10B according to a modified example.

FIG. 3 shows functional blocks of the image processing apparatus 10B according to this modified example. As shown in FIG. 3, the image processing apparatus 10B is configured to include a defect correction unit 11B, the image storage unit 13, a development unit 11C, the digital zooming and panning unit 14, and the graphic board 15.

The defect correction unit 11B and the development unit 11C are obtained by dividing functions of the defect correction and development unit 11 according to the above-mentioned embodiment into defect correction processing and development processing. The image processing apparatus 10B does not include the image compression unit 12.

Regarding a flow of processing, the image processing apparatus 10B receives a fluorescence image output from the 24M pixel camera 7 first.

The fluorescence image input to the image processing apparatus 10B is subject to defect correction processing in the defect correction unit 11B. After the defect correction processing, the fluorescence image is output to the image storage unit 13 and the development unit 11C.

The fluorescence image input to the image storage unit 13 is stored in the image storage unit 13. The function and configuration of the image storage unit 13 is the same as that in the above-mentioned embodiment.

The fluorescence image input to the development unit 11C is subject to development processing such as demosaic processing. After that, the developed fluorescence image is output to the digital zooming and panning unit 14.

After the development processing, the digital zooming and panning unit 14 performs digital zooming processing or panning processing on the fluorescence image output to the digital zooming and panning unit 14 in order to enlarge an image of only the area ROI in which the operator is interested and display the image. The function and configuration of the digital zooming and panning unit 14 is the same as that in the above-mentioned embodiment.

The fluorescence image that has been subject to processing in the digital zooming and panning unit 14 is displayed on the monitor for fluorescence image observation 16 via the graphic board 15.

Second Embodiment

Next, a second embodiment of the present disclosure will be described. The major difference between the second embodiment and the first embodiment is that the monitor for surgical field observation 3 is separated from the monitor for fluorescence image observation 16 in the first embodiment and two images are superimposed and the superimposed image is observed on a monitor in the second embodiment. It should be noted that the second embodiment is the same as the first embodiment in that the area ROI in which the operator is interested is displayed on a monitor and an image of the entire image storing area RA that may undergo surgery is stored.

Figure 4:
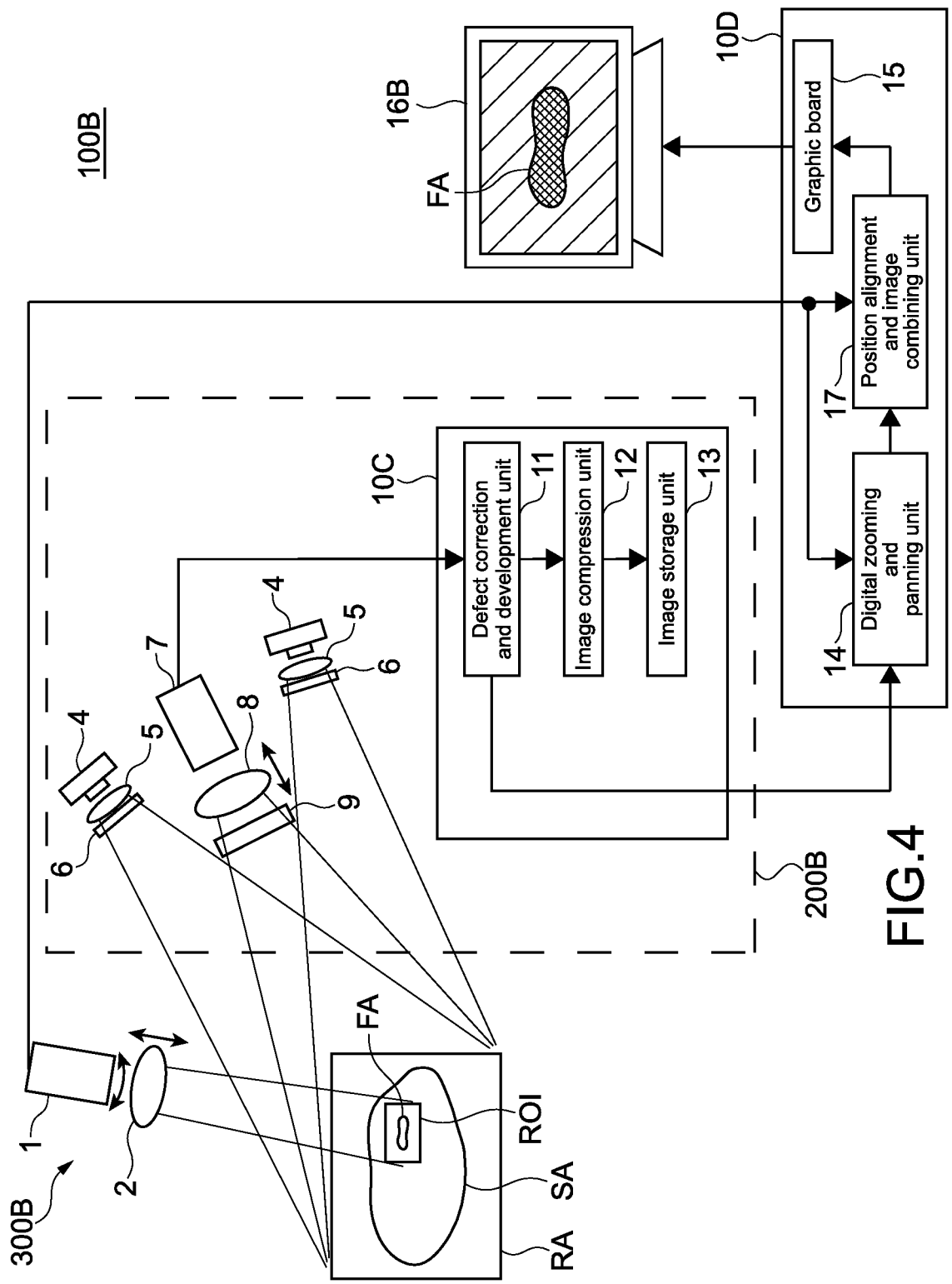
FIG. 4 is a whole configuration diagram of a fluorescence navigation surgery system 100B according to a second embodiment.

FIG. 4 shows the entire configuration of the fluorescence navigation surgery system 100B according to this embodiment. It should be noted that elements of the same functions as those according to the first embodiment will be denoted by the same reference symbols and a description thereof will be omitted.

The fluorescence navigation surgery system 100B is largely divided into a visible light capturing system 300B for the operator to observe the surgical field SA and a fluorescence capturing system 200B that captures and stores a fluorescence image. Then, a system for surgery based on the assumption that surgery is carried out while seeing an image for surgical field observation captured by the visible light capturing system 300B is assumed. Therefore, the fluorescence navigation surgery system 100B further includes an image processing apparatus 10D that aligns a display range of a fluorescence image captured by the fluorescence capturing system 200B with a display range of anÝÝthe image for surgical field observation to superimpose the images and a monitor for superimposed image observation 16B that displays the superimposed image.

(Visible Light Capturing System)

The visible light capturing system 300B is configured to include the video camera for surgical field observation 1 and the optical zoom lens 2. The video camera for surgical field observation 1 is capable of capturing an image of the entire surgical field SA, and the capturing direction thereof can be rotated, i.e., the video camera can be panned. Further, the video camera for surgical field observation 1 is capable of performing optical zooming with the optical zoom lens 2 to capture an image of only the area ROI in which the operator is interested. The image captured by the video camera for surgical field observation 1 is output to the image processing apparatus 10D.

(Fluorescence Capturing System)

On the other hand, the fluorescence capturing system 200B is configured to include the LED 4, the lens 5, the exciting filter 6, the 24M pixel camera 7, the optical zoom lens 8, the emission filter 9, and an image processing apparatus 10C.

Moreover, the image processing apparatus 10C is configured to include the defect correction and development unit 11, the image compression unit 12, and the image storage unit 13 as functional blocks.

The fluorescence image that has been subject to defect correction processing and development processing in the defect correction and development unit 11 is output to the image compression unit 12 and the digital zooming and panning unit 14 of the image processing apparatus 10D.
(Configuration of Image Processing Apparatus 10D and Flow of Processing)

The image processing apparatus 10D is configured to include functional blocks of the digital zooming and panning unit 14 and a position alignment and image combining unit 17, and the graphic board 15. It should be noted that the image processing apparatuses 10C and 10D may be constituted of a PC or a dedicated IC such as an FPGA similarly to the image processing apparatus 10 according to the first embodiment.

In the image processing apparatus 10D, the digital zooming and panning unit 14 receives a fluorescence image supplied from the defect correction and development unit 11 and information on optical zooming and panning (position selecting information) of the video camera for surgical field observation 1 supplied from the video camera for surgical field observation 1, first. The digital zooming and panning unit 14 performs digital zooming processing and digital panning processing on the fluorescence image based on the received information on optical zooming and panning to appropriately superimpose the fluorescence image with the image supplied from the video camera for surgical field observation 1. The fluorescence image that has been subject to zooming processing and panning processing is output to the position alignment and image combining unit 17.

Next, the position alignment and image combining unit 17 superimposes the image for surgical field observation supplied from the video camera for surgical field observation 1 with the fluorescence image supplied from the digital zooming and panning unit 14 and combines the images. The superimposed image thus combined is output to the monitor for superimposed image observation 16B via the graphic board 15 and is displayed on a screen with an HD.

It should be noted that in the above description, position alignment is performed based on the information on optical zooming and panning of the video camera for surgical field observation 1, which is supplied from the video camera for surgical field observation 1. However, the present disclosure is not limited thereto, and the position for superimposing images is obtained by image analysing processing such as edge detection to superimpose the images.

Hereinabove, the configuration of the second embodiment has been described. It should be noted that in the above description, the configuration in which an image for surgical field observation and a fluorescence image are superimposed and the image thus obtained is displayed on the monitor for superimposed image observation 16B has been described. However, there is a request that displays the image for surgical field observation and the fluorescence image separately on a monitor during surgery depending on the operator's taste. Therefore, also in the configuration of the second embodiment, it is possible to separately extract the image for surgical field observation output from the video camera for surgical field observation 1 and output to the monitor for surgical field observation 3 and to separately extract the fluorescence image output from the digital zooming and panning unit 14 and output to the monitor for fluorescence image observation 16.

Third Embodiment

Next, a third embodiment of the present disclosure will be described. The major difference between the third embodiment and the second embodiment is that the video camera for surgical field observation 1 and the 24M pixel camera 7 capture an image of the image storing area RA or the area ROI in which the operator is interested from different directions in the second embodiment and the image is captured from the same optical axis direction in the third embodiment.

Figure 5:
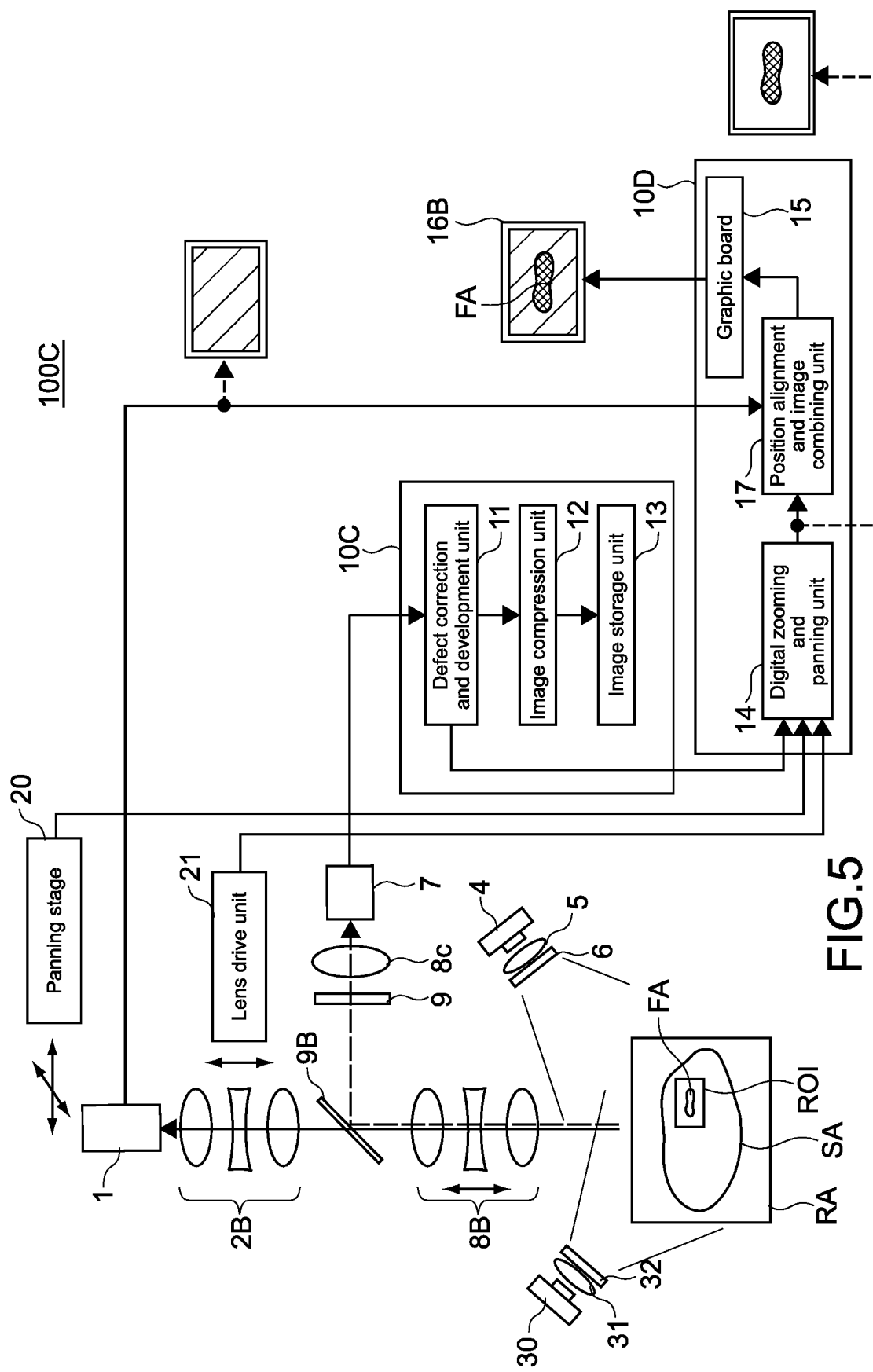
FIG. 5 is a whole configuration diagram of a fluorescence navigation surgery system 100C according to a third embodiment.

FIG. 5 is a whole configuration diagram of the fluorescence navigation surgery system 100C according to this embodiment. It should be noted that elements of the same functions as those according to the first embodiment and the second embodiment will be denoted by the same reference symbols and a description thereof will be omitted.

As described above, the fluorescence navigation surgery system 100C is a capturing system in which a visible light capturing system is integrated with a fluorescence capturing system and a part of an optical system is shared.
(Configuration and Flow of Capturing)

The capturing system is configured to include the video camera for surgical field observation 1, an optical zoom lens 2B, a lens drive unit 21, a panning stage 20, the LED 4, the lens 5, the exciting filter 6, the 24M pixel camera 7, an optical zoom lens 8C, the emission filter 9, a dichroic mirror 9B, a zoom lens 8B, a visible light LED 30, a lens 31, and a visible light filter 32.

Capturing with visible light will be described first. Visible light illumination including the visible light LED 30, the lens 31, and the visible light filter 32 applies visible light to the image storing area RA. Light that has been reflected from the image storing area RA is incident on the zoom lens 8B. The field of view of the zoom lens 8B is adjusted in the 24M pixel camera 7 in such a way that an image of the entire image storing area RA is captured. Visible light that has transmitted through the zoom lens 8B is incident on the dichroic mirror 9B. The dichroic mirror 9B is configured to reflect only fluorescence emitted from the fluorescence area FA and cause visible light to be transmitted therethrough. The visible light that has transmitted through the dichroic mirror 9B is incident on the zoom lens 2B. The zoom lens 2B is driven by the lens drive unit 21 and the field of view of the video camera for surgical field observation 1 is enlarged at a magnification that is necessary for capturing an image of the area ROI in which the operator is interested. Moreover, the field of view of the video camera for surgical field observation 1 is focused on the area ROI in which the operator is interested by panning the video camera for surgical field observation 1 by the panning stage 20.

In this way, an image of the area ROI in which the operator is interested is captured in the video camera for surgical field observation 1. The captured visible light image is output to the position alignment and image combining unit 17. Moreover, in order to focus the field of view on only the area ROI in which the operator is interested, information on zooming performed by the lens drive unit 21 and panning performed by the panning stage 20 is output to the digital zooming and panning unit 14 as information on optical zooming and panning (position selecting information).

Next, capturing with fluorescence will be described. The fluorescence area FA glows with excitation light emitted from an excitation light source including the LED 4, the lens 5, and the exciting filter 6. The fluorescence emitted from the fluorescence area FA is transmitted through the zoom lens 8B whose field of view is adjusted in such a way that an image of the entire image storing area RA is captured, is reflected by the dichroic mirror 9B, is transmitted through the emission filter 9 and the optical zoom lens 8C, is incident on the 24M pixel camera 7, and is captured.

In this way, a fluorescence image of the entire image storing area RA is captured by the 24M pixel camera 7. The captured fluorescence image is output to the defect correction and development unit 11.

With the above-mentioned configuration, it is possible to capture a visible light image and a fluorescence image from the same direction. Therefore, the position alignment in the position alignment and image combining unit 17 can be easily performed, and it is possible to accurately align positions of two types of images and to superimpose the images.

Hereinabove, the third embodiment has been described.

(Supplementary Note)

In addition, embodiments of the present technology are not limited to the above-mentioned embodiments and various modifications can be made without departing from the gist of the present technology.

It should be understood by those skilled in the art that various modifications, combinations, sub-combinations and alterations may occur depending on design requirements and other factors insofar as they are within the scope of the appended claims or the equivalents thereof.

What is claimed is:

1. A surgical navigation system for use during surgical operation, comprising:
    a surgical microscope including:
        at least one light source device configured to apply excitation light to an observation target of a living body;
        a fluorescent imaging device configured to capture a fluorescent image of the observation target based on excitation light reflected from the observation target, the fluorescent image having a first pixel resolution; and
        a visible light imaging device configured to capture a visible light image of the observation target, the visible light imaging device having a red, green, and blue (RGB) color filter pattern and generating the visible light image as a color image according to a demosaicing process;
    a display having a second pixel resolution different from the first pixel resolution; and
    circuitry configured to:
        receive selecting information about a partial area of the observation target that corresponds to a defect corrected and uncompressed region of interest (ROI), the selecting information including information on at least one of zooming or panning performed by the visible light imaging device when capturing the visible light image of the observation target;
        select a portion of the fluorescent image based on the selecting information;
        generate a superimposed image by aligning the selected portion of the fluorescent image with the visible light image; and
        control the display to display the superimposed image with the ROI.

2. The surgical navigation system of claim 1, further comprising:
    an optical device that directs the excitation light toward the fluorescent imaging device and that directs the visible light toward the visible imaging device.

3. The surgical navigation system of claim 2, wherein the optical device reflects the excitation light and passes the visible light.

4. The surgical navigation system of claim 2, wherein the optical device comprises a dichroic mirror.

5. The surgical navigation system of claim 1, wherein the selecting information includes edge information of the visible light image.

6. The surgical navigation system of claim 1, further comprising:
    a first zoomable lens optically coupled to the visible light imaging device; and
    a second zoomable lens optically coupled to the fluorescent imaging device.

* * * * *